(12) United States Patent
Ni et al.

(10) Patent No.: US 11,904,182 B2
(45) Date of Patent: Feb. 20, 2024

(54) RESEARCH AND DEVELOPMENT OF AUGMENTED REALITY IN RADIOTHERAPY

(71) Applicant: CHANGZHOU NO.2 PEOPLE'S HOSPITAL, Jiangsu Province (CN)

(72) Inventors: Xinye Ni, Jiangsu Province (CN); Chunying Li, Jiangsu Province (CN); Zhengda Lu, Jiangsu Province (CN); Kai Xie, Jiangsu Province (CN); Lei Li, Jiangsu Province (CN); Zhiyin Zhu, Jiangsu Province (CN); Tao Wang, Jiangsu Province (CN)

(73) Assignee: CHANGZHOU NO. 2 PEOPLE'S HOSPITAL, Jiangsu Province (CN)

( * ) Notice: Subject to any disclaimer, the term of this patent is extended or adjusted under 35 U.S.C. 154(b) by 176 days.

(21) Appl. No.: 17/117,856

(22) Filed: Dec. 10, 2020

(65) Prior Publication Data

US 2021/0379406 A1 Dec. 9, 2021

(30) Foreign Application Priority Data

Jun. 4, 2020 (CN) .......................... 202010498208.6

(51) Int. Cl.
*G06T 7/73* (2017.01)
*G06T 13/20* (2011.01)
(Continued)

(52) U.S. Cl.
CPC ........... *A61N 5/1039* (2013.01); *A61N 5/107* (2013.01); *G06T 7/75* (2017.01); *G06T 13/20* (2013.01);
(Continued)

(58) Field of Classification Search
CPC .... G06T 7/70; G06T 7/73; G06T 7/75; G06T 13/20; G06T 17/00; G06T 19/006;
(Continued)

(56) References Cited

U.S. PATENT DOCUMENTS

| 2010/0149174 A1* | 6/2010 | Nakao | ..................... A61B 6/466 |
| | | | 345/419 |
| 2011/0224546 A1* | 9/2011 | Lee | ..................... A61B 8/0866 |
| | | | 600/443 |

(Continued)

OTHER PUBLICATIONS

Nyman, Maria Hälleberg, et al. "Patients' perspective on participation in care with or without the support of a smartphone app during radiotherapy for prostate cancer: qualitative study." JMIR mHealth and uHealth 5.7 (2017): e6829. (Year: 2017).*

(Continued)

*Primary Examiner* — Diane M Wills
(74) *Attorney, Agent, or Firm* — TAROLLI, SUNDHEIM, COVELL & TUMMINO L.L.P

(57) ABSTRACT

A method is provided of producing an optical filter. The method comprises depositing a first mirror layer onto a substrate; depositing an insulating layer on the first mirror; exposing at least some of a plurality of portions of a surface of the insulating layer to a dose of energy; developing the insulating layer in order to remove a volume from the at least some of the plurality of portions of the insulating layer, wherein the volume of the insulating layer removed from each portion is related to the dose of energy exposed to each portion, and wherein a remaining thickness after the removal of the volume from each portion of the insulating layer is related to the dose of energy exposed to each portion. The method further comprising depositing a second mirror layer on the remaining thickness of each of the plurality of portions of the insulating layer.

6 Claims, 5 Drawing Sheets

(51) Int. Cl.
*G06T 17/00* (2006.01)
*G06T 19/00* (2011.01)
*G06T 19/20* (2011.01)
*A61N 5/10* (2006.01)
*G16H 20/40* (2018.01)
*G16H 30/20* (2018.01)

(52) U.S. Cl.
CPC ............ *G06T 17/00* (2013.01); *G06T 19/006* (2013.01); *G06T 19/20* (2013.01); *G16H 20/40* (2018.01); *G16H 30/20* (2018.01); *A61N 2005/105* (2013.01); *A61N 2005/1059* (2013.01); *A61N 2005/1072* (2013.01); *G06T 2207/30196* (2013.01); *G06T 2210/41* (2013.01); *G06T 2210/62* (2013.01); *G06T 2213/08* (2013.01); *G06T 2219/2004* (2013.01); *G06T 2219/2016* (2013.01)

(58) Field of Classification Search
CPC ............ G06T 19/20; G06T 2219/2004; G06T 2210/62; G06T 2213/08; G06T 2219/2016; G06T 2207/30196; G06T 2210/41; G06H 30/00; G06H 30/20; A61N 5/1039; A61N 5/107; A61N 5/1031; A61N 2005/105; A61N 5/1049; A61N 2005/1072
See application file for complete search history.

(56) References Cited

U.S. PATENT DOCUMENTS

| | | | |
|---|---|---|---|
| 2016/0023019 A1* | 1/2016 | Filiberti | A61N 5/107 600/1 |
| 2019/0240508 A1* | 8/2019 | Friman | G06F 3/0346 |
| 2020/0054398 A1* | 2/2020 | Kovtun | G16H 40/63 |
| 2020/0375661 A1* | 12/2020 | Veigel | G09B 19/003 |

OTHER PUBLICATIONS

Wiencierz, Manfred, Kathrin Kruppa, and Lutz Lüdemann. "Clinical validation of two surface imaging systems for patient positioning in percutaneous radiotherapy." arXiv preprint arXiv:1602.03749 (2016). (Year: 2016).*

Guo W, Müller-Polyzou R, Chen Z, Meier N, Georgiadis A. Patient Positioning in Radiotherapy. In2020 IEEE International Symposium on Medical Measurements and Applications (MeMeA) Jun. 1, 2020 (pp. 1-6). IEEE (Year: 2020).*

* cited by examiner (a)

(b)

RESEARCH AND DEVELOPMENT OF AUGMENTED REALITY IN RADIOTHERAPY

RELATED APPLICATIONS

The present invention is a Nonprovisional Application under 35 USC 111(a), claiming priority to Serial No. CN 202010498208.6, filed on 4 Jun. 2020, the entirety of which is incorporated herein by reference.

FIELD OF INVENTION

The present invention relates to the technical field of radiotherapy, in particular to the research and development technology of augmented reality in radiotherapy.

BACKGROUND OF INVENTION

Description of the Related Art

Radiotherapy is one of the three major measures for the clinical treatment of tumors, and a vast majority of patients with malignant tumors need to receive radiotherapy in their treatment. The purpose of radiotherapy is to maximize the destruction of tumor cells and protect the surrounding normal tissues and organs from radiation exposure. Studies have shown that an inaccurate positioning of a patient during radiotherapy will greatly increase the patient's recurrence rate. However, it is very difficult to determine the accuracy of positioning for the reasons such as a large number of radiotherapy, a long cycle, and many other influencing factors.

At present, the main process used for radiotherapy positioning includes: (1) Scan Positioning: The positioning is performed on a CT couch according to the body position elements required by radiotherapy, and the body position elements are fixed according to a patient's conditions and parts. Highly repeatable body positions are selected, and holders are used for the fixation. The holder is usually a face mask or a vacuum pillow used for the patient's head and neck, and a body frame or a vacuum pad for the patient's body. (2) Drawing a Positioning Line Mark: A body position element marking line is marked as close to the tumor area as possible in order to maintain the consistency of the patient's body position elements in the CT positioning scan and radiotherapy. A horizontal line is marked on the patient's skin near the midline of the body through a laser cross-line on both sides of the CT, and the laser cross-line at the ceiling is provided for marking a vertical line on the skin at the center of the patient's body. (3) CT Scan: This scan is performed at a required corresponding part of the patient according to a treatment plan, and then a CT scan IMAGE is obtained and transmitted to a treatment plan workstation. (4) Delineation of Target Area and Normal Tissue: A target area and normal tissues around the target area are confirmed in front of a computer image of a treatment planning system (TPS) by a doctor. In other words, the tumor area requiring radiotherapy and the normal tissues requiring protection are confirmed. (5) Plan Design and Evaluation: The prescription dose for the target area and the protective dose for the normal tissues are confirmed by a radiotherapy doctor, and a radiotherapist carries out the radiotherapy plan according to the requirements of the plan, and this plan includes parameters such as an irradiation method, the quantity of shooting fields, the direction of the shooting field, etc. After the results of different treatment plans are produced, the doctor confirms and selects the best treatment plan. (6) Patient's Actual Treatment Center Mark: The TPS computes the spatial position relation between the mark point on skin and the isocenter of treatment (which is often the center of a tumor) in the positioning process, and a mark point of the isocenter of treatment is marked on the patient's body surface. (7) Position Verification: Before the treatment, the patient requires a CBCT scan, and an X-ray tube in a KV scale installed on the accelerator is provided for scanning a patient positioned at a positioning element by a cone beam formed by a field collimator, and matching the CT scan IMAGE of the treatment plan to directly obtain a margin of error between the actual positioning and the positioning element according to the treatment plan, so that a radiation therapy technician can make related adjustments according to the margin of error before performing the scan. (8) Dose Verification: This verification is required for some patients before the radiotherapy takes place in order to confirm whether or not the patient's actual exposure dose is the same as the dose specified by the treatment plan. In general, a phantom is used to substitute the human measurement of the patient, and the contents of the measurement mainly include an absolute dose measurement and a relative dose measurement, and these measurements are compared with the plan. If these measurements fail to comply with the plan, then it will be necessary to find out the reasons or even to redesign the radiotherapy plan.

In radiotherapy positioning, there are two main problems as described below: (1) Respiratory movement and voluntary movement of other tissues cause movements of tumor tissues, and this problem is mainly concentrated at the patient's chest and abdomen, but the respiratory movement affects the patient's head and neck relatively less. In the current treatment method, the target area for radiation is usually increased to provide a one-time full-coverage radiation treatment, but this method obviously increases the radiation damage to the surrounding normal tissues. (2) During the process of 30 to 40 days of radiotherapy, the patient's body will undergo some changes, and the tumor will also undergo some changes, and these changes will bring a certain deviation. At present, this problem can only be solved by scanning the image again and again to obtain more updated information and then apply feasible solutions stage by stage.

During the process of radiotherapy, negligence at work may lead to the following series consequences: (1) The treatment plan is carried out without checking the plan list carefully. For example, the treatment plan for Patient A may be applied on Patient B; (2) The same patient needs different treatment plans for different parts of the body, and sometimes the treatment plan for Part A may be applied on Part B.

SUMMARY OF THE INVENTION

Therefore, it is a primary objective of the present invention to overcome the drawbacks of the prior art by providing a research and development of augmented reality in radiotherapy in accordance with the present invention.

To achieve the aforementioned and other objectives, the present invention discloses a research and development of augmented reality in radiotherapy, and it comprises the following steps (S1~S8):

(S1) Image Scan: CT scan of a patient is performed to obtain a DICOM image.

(S2) Preparation of Radiotherapy Plan: The DICOM data obtained in the step (S1) is inputted into a treatment planning system, and a delineation of a planning target volume, a clinical target volume, and surrounding vital organs and tissues is carried out by a radiotherapist, and a virtual cube with the same dimensions (such as 16 cm*16 cm*16 cm) of the cube calibration module (As shown in FIG. 7) is delineated, and the center of the virtual cube is set at an isocenter position in TPS, and a DICOM-RT data set is outputted.

(S3) Construction of Model: The DICOM-RT data delineated in the step (S2) are inputted into a medical image processing software to carry out a three-dimensional reconstruction, and a certain transparency in the model is used to show a contour of body surface, a planning target volume, a clinical target volume and other surrounding organs and tissues, and then a 3D model Is outputted in a common 3D processing software usable format, so as to complete the conversion of the medical data image into the 3D software usable format.

(S4) Art Processing: 3D animation production software is used to make a material adjustment of a human 3D model, and then an augmented reality application program development software is introduced to adjust a material texture, and a light adjustment of the whole scene is made in the software.

(S5) Building of System: An augmented reality interactive system is built, and the 3D virtual model is used to reduce a real scene, and then a real-time object motion is driven in a 3D environment to achieve an augmented reality simulation at the mobile end.

(S6) Programming and internal testing: Using a programming language to carry out functional programming in the augmented reality application development software, positioning the 3D virtual model in the system, and realizing the translation and rotation of the X, Y and Z axis of the 3D virtual model. Before use, the project file packaged and generated into a program file is tested in a mobile device internally to ensure a stable fluency of the program.

(S7) Positioning a Virtual Model: The virtual cube and six-dimensional alignment method of the cube calibration module are used to realize the spatial position consistency between the 3D virtual model and the linear accelerator, in order to ensure that the 3D virtual model is positioned at the isocenter position.

(S8) Clinical Application: Before the patient lies in a treatment couch of the accelerator, the cube calibration module is placed, and a tablet device is used to identify the object and perform an interactive operation of the 3D virtual model, so that after the 3D virtual model is positioned at the isocenter of the accelerator, the cube calibration module is removed. The patient is clinically treated lies in the treatment couch of the accelerator, and the couch is lifted, translated, and rotated according to the positioning requirement of the radiotherapy to appropriately adjust the patient's treatment body position, and match with the space of the early-stage 3D virtual model, so that patient's body contour and the 3D virtual model in a high degree. At this time, open the virtual field for verification.

Preferably, the scene is rendered and baked in the step (S4).

Preferably, the mobile end comprises a tablet device in the step (S5).

Preferably, the step performed between the 3D virtual model in a space matching in the step (S8) specifically includes a body contour matching.

Preferably, the treatment couch parameters and the patient's body position are adjusted appropriately in the step (S8).

Preferably, an apparatus for the application of augmented reality in radiotherapy comprises a plurality of radiotherapy devices including an accelerator, and a 6D treatment couch, and a at least one tablet device comprise a motion sensor, a laser radar scanner, a mobile device and a corresponding supporting device of a camera.

Compared with the prior art, the present invention uses the augmented reality technology to achieve the positioning effect free of radiation and with the advantages of visualization, and the invention is capable of displaying the contour of human body, major organs and tissues, tumor tissues, planning target volume (PTV), etc. on a display device, and the patient is aligned precisely with the 3D virtual model to compensate the errors in the process of a conventional positioning process. According the positioning of radiotherapy, the couch is lifted, translated and rotated to appropriately adjust the patient's treatment body position and match (particularly the patient's body contour) with the space of the early-stage 3D virtual model. At this time, open the virtual radiation field for verification and indicators are observed visually to determine whether a tumor position falls within a treatment field or at an isocenter. If there is a deviation between the two (the real human body and the virtual 3D model), the treatment couch parameters and the patient's body position will be adjusted, to match the patient's body contour and the virtual model in a high degree before carrying out the radiotherapy treatment.

BRIEF DESCRIPTION OF THE DRAWINGS

FIG. 9(a) is shot at the bedside. It can be seen that the virtual radiation field (purple) is completely included in PTV (green). FIG. 9(b) is shot at the end of the couch and the simulated beam can be seen.

DESCRIPTION OF THE PREFERRED EMBODIMENTS

Figure 1:
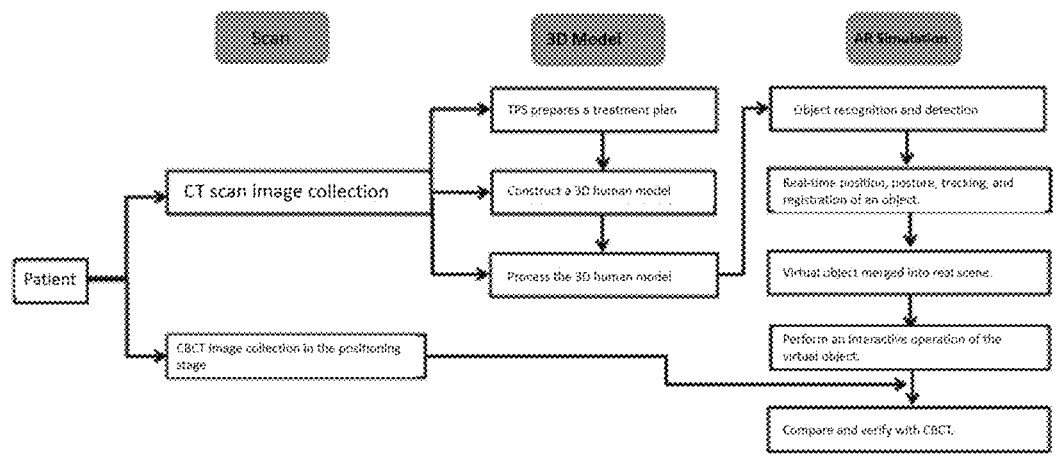
FIG. 1 is a flow chart of a research and development of augmented reality in radiotherapy in accordance with the present invention.

The technical characteristics of the present invention will become apparent in the following detailed description of the preferred embodiments with reference to the accompanying drawings. It is noteworthy that the embodiments are provided for the purpose of illustrating the present invention, but not intended for limiting the scope of the invention.

With reference to FIGS. 1 to 9 for a research and development of augmented reality in radiotherapy, the application comprises the following steps (S1 to S8):

(S1) Image Scan: CT scan of a patient is performed to obtain a DICOM image.

(S2) Preparation of Radiotherapy Plan: The DICOM data obtained in the step (S1) are inputted into a treatment planning system (TPS), and a delineation of a planning target volume (PTV), a clinical target volume (CTV), and surrounding vital organs and tissues is carried out by a radiotherapist, and a virtual cube of (16 cm*16 cm*16 cm) situated at the isocenter is produced to achieve the calibration of the isocenter, and such information is outputted as a DICOM-RT data set.

(S3) Construction of Model: The DICOM-RT data delineated in the step (S2) are inputted into a medical image processing software to carry out a three-dimensional reconstruction, and a certain transparency in the model is used to show a contour of body surface, a planning target volume (PTV), a clinical target volume (CTV) and other surrounding organs and tissues, and then a 3D model is outputted in a common 3D processing software usable format in order to achieve the data compatibility and conversion between the CT human data and 3D software and the augmented reality application program development software.

(S4) Art Processing: 3D animation production software is used to make a material adjustment of a human 3D virtual model, and then an augmented reality application program development software is introduced to adjust a material texture, and a light adjustment of the whole scene is made in the software. At the same time, the virtual radiation field is constructed by using the information of radiation field. Finally, the scene is rendered and baked to ensure the smooth operation of the whole scene.

(S5) Building of System: An augmented reality interactive system is built, and the 3D virtual model is used to reduce a real scene, and then a real-time object motion is driven in a three-dimensional environment to achieve an augmented reality simulation at the mobile end such as a mobile phone or a tablet PC.

(S6) Programming and internal testing: Using a programming language to carry out functional programming in the augmented reality application development software, positioning the 3D virtual model in the system, and realizing the translation and rotation of the X, Y and Z axis of the 3D virtual model. Before use, the project file packaged and generated into a program file is tested internally in a mobile device to ensure a stable fluency of the program.

(S7) Positioning a Virtual Model: A virtual cube of the virtual model and six-dimensional alignment method of the cube calibration module are used to realize the spatial position consistency between the 3D virtual model and the linear accelerator and ensure that the 3D virtual model is positioned at the isocenter position.

(S8) Clinical Application: The cube calibration module is removed, and the patient to be treated clinically lies in a treatment couch of the accelerator, and the couch is lifted, translated, and rotated according to the positioning requirement of the radiotherapy to appropriately adjust the patient's treatment body position, and match with the space of the early-stage 3D virtual model and particularly match the patient's body contour with the space of the early-stage 3D virtual model. At this time, open the virtual radiation field for verification and visually observe indicators to determine whether a tumor position falls within a treatment radiation field or at an isocenter. If there is a deviation between reality and virtuality, the treatment couch parameters and the patient's body position can be adjusted to match the patient's body contour and the virtual model in a high degree before carrying out the radiotherapy treatment.

By observing a patient (such as a breast cancer patient) who breathes to a specific position (indicated by the contour of body surface) and compares such position with the contour of the treatment plan, an active or passive method to hold the breath to perform the radiotherapy when there is a match. After a specific time, the patient breathes freely to repeat the process by holding the breath and perform the radiotherapy again. The irradiation will be stopped immediately when the contour of the body surface in not consistent with the planned contour.

Wherein, it is necessary to render and bake the scene in the step (S4). The mobile end includes a tablet device in the step (S5). The 3D virtual model used for performing a space matching in the step (S8) specifically performs a body contour matching, and the treatment couch parameters and the patient's body position are adjusted appropriately in (S8).

Figure 2:
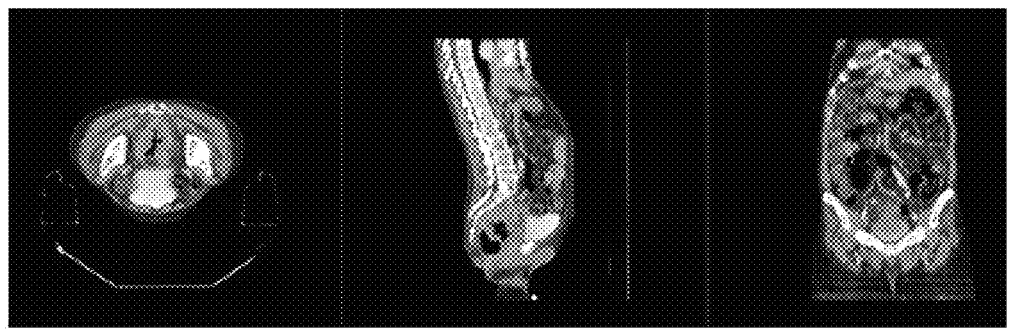
FIG. 2 shows the data of a patient's CT scan in a horizontal plane, a coronal plane and a sagittal plane respectively.

In an embodiment, the operation procedure is described as follows:

(S1) CT Scan:

The CT scan is carried out at a horizontal plane, a coronal plane, and a sagittal plane of a patient, wherein the scan voltage is 120 KV, the effective tube current is 20 mA, the reconstruction layer thickness is 5 mm, and CT images as shown in FIG. 2 are obtained.

(S2) Preparation of Radiotherapy Plan

Preparing the radiotherapy plan is an important step to achieve a precise radiotherapy, and its principle is to kill tumor cells as many as possible and protect the normal tissues and vital organs as much as possible.

After a patient's positioning scan image data are processed preliminarily, and a discussion between a radiotherapy doctor and a radiotherapist have been made, a contour of the radiotherapy target area and the vital organs and tissues needed to be protected is delineated. The radiotherapy target area includes a gloss tumor volume (GTV), and a clinical target volume (CTV) which is a subclinical foci invaded by the GTV and the tumor, a planning target volume (PTV) which is a patient's CTV with an error of organ movement and positioning.

Figure 3:
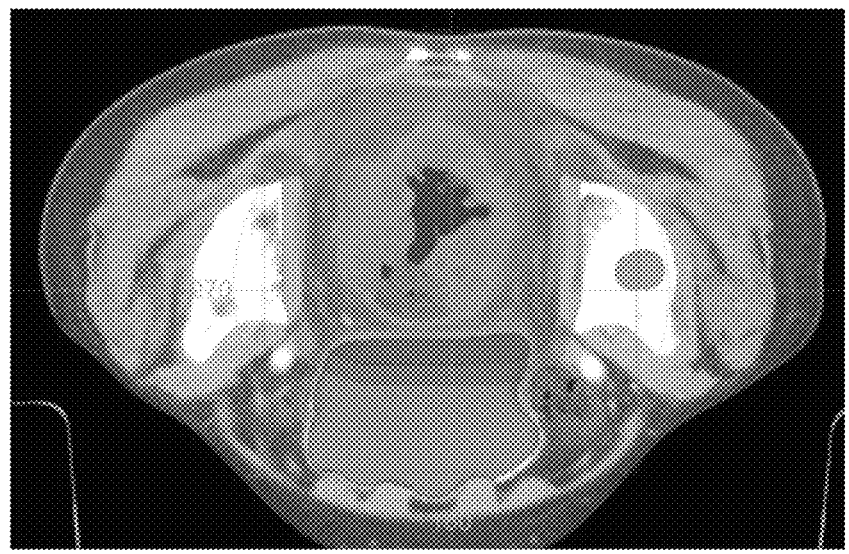
FIG. 3 shows a planning target volume (PTV), a clinical target volume (CTV), surrounding organs and tissues, and a field marking line delineated after a patient's DICOM data processed by a treatment planning system (TPS), wherein the calibration of an isocenter is achieved, and a virtual cube of 16 cm*16 cm*16 cm is produced at the isocenter, and such information is outputted as a DICOM-RT data set.

After the delineation of the radiotherapy target area and the contour of vital organs and tissues required to be protected is completed, the radiotherapist designs the field defining and field arrangement according to a TPS planning system and uses tools such as a DVH curve and a measurement curve to evaluate the plan, and finalizes the radiotherapy plan. To set the 3D virtual model at the isocenter later, we also sketch a virtual cube with the same dimensions (16 cm*16 cm*16 cm) of the cube calibration module at the isocenter as shown in FIG. 3;

(S3) Model Construction

Figure 4:
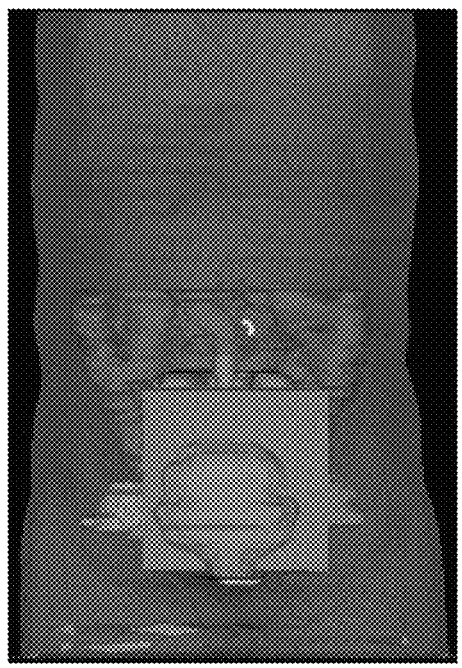
FIG. 4 shows the steps of carrying out a three-dimensional reconstruction of a DICOM-RT data set by using a medical image processing software and outputting the data in a common 3D software usable format.
Figure 5:
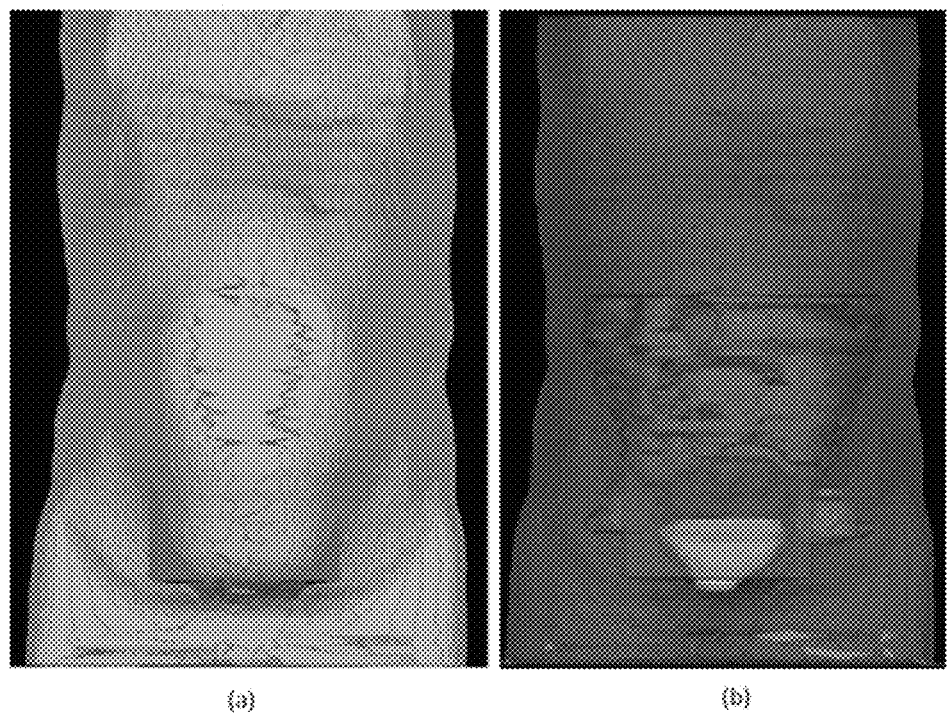
FIG. 5 shows the photos of making a material adjustment of a 3D model by using a 3D animation software.

The DICOM-RT data set prepared after the radiotherapy plan is inputted into a medical image processing software to achieve an export of the exchange data of a commercial RT plan system and the visualization of structure, dose distribution and treatment plan as shown in FIG. 4. The processed data of the model are save into different format and inputted into a 3D animation software, and it is found that the data of the model in the .stl format retain the relative positions of each organ/tissue and the target area, and also retain the name information of each model, so that the model in the .stl format is selected for export;

(S4) Model Optimization and Processing

The model in the .stl format is introduced into the 3D animation software. In FIG. 5(a), the model is unable to retain the material information and the rendering effect in the medical image processing software, so that a material adjustment of the model is made in the 3D animation software. In FIG. 5(b), the target area of each organ is shown by an appropriately transparency to ensure the visual effect of the model. At the same time, the virtual radiation field is constructed by using the information of radiation field.

(S5) Constructing an Augmented Reality Simulation System

The human 3D virtual model is introduced into an augmented reality application program development software for the development of an augmented reality simulation system.

The present invention also discloses an apparatus for a research and development of augmented reality in radiotherapy, and the apparatus comprises radiotherapy devices including an accelerator, and a six-dimensional machine tool, and the at least one tablet device comprise a motion sensor, a laser radar scanner, a mobile device and a corresponding supporting device of a camera.

Wherein, the camera equipment with ultra-high picture elements adopts an ultra-wide angle function to obtain a larger field, and such camera comes with a very strong photosensitivity to improve the image quality in a low-light condition. In a laser radar scanner, a transmitter emits laser and a receiver the light reflected from an object, and a dToF technology is used to calculate the process of light from emission to reception, so as to obtain the information of distance and depth from the laser radar scanner to the object. The image information obtained by the camera, the depth information obtained by the laser scanner, and the information captured by the motion sensor are combined, and a computer vision algorithm is used to understand a scene.

Further, the augmented reality application program development software applied in the present invention is used to build an augmented reality interactive system. In the main process, the 3D virtual model reduces a real scene, and then an object motion is driven instantly in a 3D environment to achieve an augmented reality simulation of a mobile end such as a mobile phone or a tablet PC. In a specific method, a camera, a laser radar scanner, a motion sensor are used to invoke the simultaneous localization and mapping system (SIMULTANEOUS Localization and Mapping (SLAM)) and position a human model in a real space, so as to achieve the effect of merging the virtual human data with the real space and render human data into the captured real world.

Further, a feature point detection technology used in this experiment mainly compares a position with a drastic change of grayscale of a captured camera image, and many feature points form a feature point cloud, and the feature points allow us to understand that device relative to the location of the user's surrounding environment.

Further, an object recognition technology used in this experiment mainly extracts a spatial feature point, wherein a spatial feature refers to a mutual relation of the spatial position or direction of several targets divided from an image, and a common method of extracting the spatial feature is to divide the image and then create an index between the features after the features are extracted. The extracted feature point is mainly a point with a drastic change of the grayscale value or a point at an edge and having a larger curvature, so that a recognition word of a different shape can be set on each plane of the cube calibration module to increase the number of recognized feature points.

Further, a device tracking used in this experiment is to use the match of a camera of an augmented reality application program development software with a camera of a device to match the real space with the virtual space, so as to complete the tracking of the real world. In other words, if the mobile device has a perspective change, the relative positions of the virtual object and the real environment should remain unchanged, and the virtual object exists on the mobile device, so that we need to estimate a change of the relative spatial position of a mobile device accurately. The main tracking technologies used include an inertial measurement unit system, a visual-inertial odometry system, and a simultaneous localization and mapping system.

Inertial measuring unit (IMU) is comprised of an accelerator and a gyroscope and used to track a user's posture, and it provides precise dead reckoning to determine a measurement scale, and carries out the steps of providing measured values of acceleration and time, calculating speed by backward integration, and then performing integration to obtains the displacement between IMU frames by again. A pure visual estimation method will cause the problem of a non-alignment between the estimated posture and the direction of gravity, and the IMU system can solve this problem very well. Firstly, the pose sequence estimated by the IMU and the pose sequence estimated by the camera are aligned precisely to estimate the true scale of the camera track, and the IMU can predict the position element of the image frame and the position of the feature point at the previous moment in the next image frame very well to improve the matching speed of the feature selection algorithm and the robustness of the corresponding quick rotation algorithm. Finally, the gravity vector provided by the accelerator in the IMU can convert the estimated location into a world coordinate system required by actual navigation.

Visual inertial odometry (VIO) combines a visual tracking system and an inertial tracking system to realize a correct correspondence between a real treatment room space and a virtual 3D model. The VIO technology can instantly track the position of an iOS device in a space, and the moving distance of the iOS device in the space can be tracked in form of a 6D space, wherein the 6D refers to an addition of 3D movements (pitch, yaw, and roll) to the xyz movements in the 3D world. In the VIO technology, information of the motion sensing hardware from the IOS device and computer vision analysis information of the visible scene of a video camera are combined during the process of creating a correspondence between the virtual and real spaces, so as to identify obvious features other than the scene ground or level ground, and then track the distance between these feature points, and compare the distance information with the motion sensing data, and finally generate a virtual model.

A simultaneous localization and mapping (SLAM) system can recognize the spatial position of a device and a position relative to various indoor obstacles and also can recognize the shape of an object such as an indoor treatment couch, an accelerator, etc. The SLAM uses a laser radar sensor to measure the angle and distance of an obstacle point around the device with very high precision and fast speed and achieve a real-time monitoring function. The SLAM uses a depth camera sensor to record depth information, and projects a light onto a surface of a surrounding object, and then measure the information of reflection to calculate the distance, and the depth camera also uses the observed information of the surrounding to estimate the position, posture and motion track of a surrounding object, and create a map according to the position elements to achieve the effects of positioning and mapping simultaneously.

Figure 6:
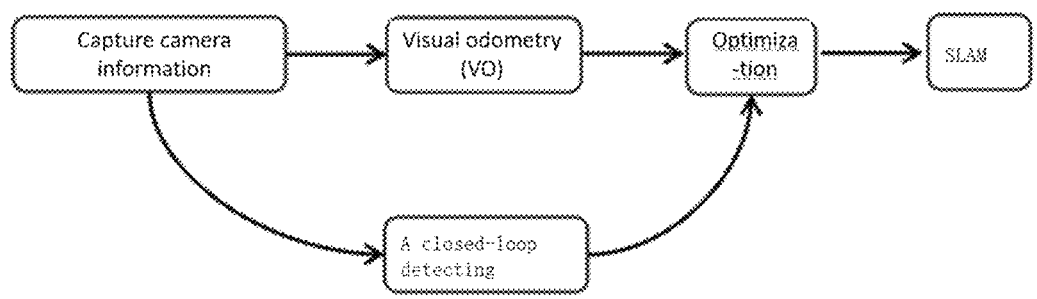
FIG. 6 is a flow chart showing the main process of achieving an instant positioning and a map construction system (SLAM)
Figure 7:
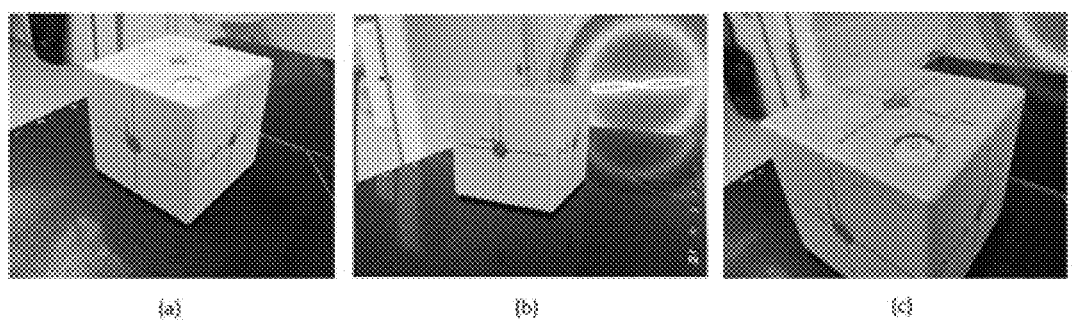
FIG. 7 shows a cube calibration module used to ensure the consistency between the spatial position between a 3D virtual model and a linear accelerator in accordance with the present invention.

The process as shown in FIG. 6 comprises camera information reading, visual odometry (VO), optimization, loop closure detection, and map building.

The camera information is mainly obtained from frames of the images captured by the camera, so that the data and information of the environment can be obtained.

The visual odometry (VO) mainly uses the image information captured by the camera to calculate the positions elements of the video camera and study two adjacent frames of images to calculate the movement of the camera between two frames, and the VO includes image feature points, the matching of feature points, and the calculation of the position elements of the camera. The image feature point includes the extraction of feature points and the feature point descriptor. In the extraction of feature points, when the position of a feature point is detected in an image, it is insufficient to match the features points just by the positions of the feature points, so that it is necessary to use the feature point descriptor to improve the matched information. The feature point descriptor can eliminate the change of scale and direction caused by different observation angles very well. When the immediacy of the extraction of feature points is taken into account, a FAST algorithm is usually used to extract the feature points. The feature matching is performed based on the feature point descriptor, wherein the distance between two feature descriptors can be used to calculate their degree of similarity, so as to find out the most similar point and complete the matching. In other words, each feature point of the previous frame is compared with the descriptor of each feature point of the next frame, and the Hamming distance is used to calculate the degree of similarity of two descriptors. If the distance is smaller than twice of the minimum distance, then we will believe the match is successful, and if the distance is greater than twice of the minimum distance, then we will believe that there is a mismatch. After the matching of feature points is completed, a camera projects a model conversion, and then the position of the feature point in a camera coordinate system is obtained, and the conversion of coordinates of a three-dimensional rigid body motion can convert a position in the camera coordinate system into a position in the world coordinate system according to the following equation:

$$p_c = R_{cw} p_w + t_{cw}$$

Wherein, $p_c$ is the coordinate of the feature point p in the camera coordinate system, $p_w$ is the coordinate in the world coordinate system, $R_{cw}$ is a rotation matrix describing a conversion from the world coordinate system into a rotation in the camera coordinate system, and $t_{cw}$ is a translation vector describing a conversion from the world coordinate system into a translation in the camera coordinate system.

After the position and depth information are obtained, an iterative closest point (ICP) algorithm is used to find a current pose.

Using the VO to calculate the camera pose may lead to a certain error. If the errors are accumulated, there will be a relatively large deviation, so that it is necessary for the rear end to optimize the front end to obtain an optimal pose. The main method is to construct a least square problem for the camera pose and a landmark point, and use a graph optimization method to construct a map. In other words, a pose is used as a vertex, and the relation between poses is used as an edge, and then the map is optimized. In other words, the pose vertex is used to satisfy the limitation of the edge, so as to minimize the error.

As time goes by, SLAM errors continue to accumulate and lead to a drift. Now, the loop closure detection is definitely necessary. In a loop closure detection, a loop closing of the map occurs when the machine recognizes a previously visited location, and the currently generated map is matched with the previously generated map to reduce the cumulative error significantly and carry out obstacle avoidance and navigation work more precisely and quickly. Finally, a map construction is carried out according to the foregoing obtained data and information.

Further, the estimated illumination for this experiment can be used to estimate the brightness and chroma of a virtual content according to the illumination of an actual environment, so as to combine the virtual world with the real world more realistically.

Further, the ray collision technology applied to this experiment is mainly used to confirm the positioning of a virtual object. When a ray is intersected with a plane in the real world that is detected by an AR device, the virtual object can be positioned.

(S6) Calibration between virtual model and linear accelerator

After the design of the augmented reality system is completed, the positioning of the 3D virtual model in actual space is random. To achieve the positioning of the 3D virtual model at the position of the isocenter, the consistency of the spatial position between the 3D virtual model and the linear accelerator must be guaranteed.

The cube calibration module applied in the present invention achieve the effects of maintaining the consistence of the spatial position between the 3D virtual model and the linear accelerator as shown in FIG. 7(a). The cube calibration module is placed on the treatment couch, and the laser positioning line is turned on, so that the laser positioning line is aligned precisely with the calibration line of the cube calibration module as shown in FIG. 7(b). Now, the isocenter is the center point among the three circular mark points as shown in FIG. 7(c). The virtual cube of the same size is produced in the 3D virtual model and aligned precisely with the cube calibration module in six dimensions to achieve the effect of precisely aligning the 3D virtual model with the isocenter of the accelerator. Now, the mobile device is fixed to this position, so that the 3D virtual model is also fixed to this position.

(S7) Clinical Application

Figure 8:
FIG. 8 shows a matching effect of an actual patient and a virtual model under the interactive design of object recognition.
Figure 9:
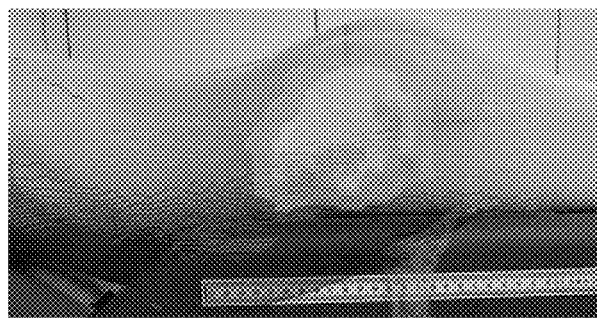
FIG. 9 shows the verification of the virtual radiation field.
Figure 9:

After the cube calibration module is removed, the patient lies on the treatment couch acts as a positioning element provided that the 3D virtual model is used as a standard. When the actual patient and the 3D virtual model in a 6D space (3D motions in xyz directions plus the pitch, yaw, and roll) has an error not exceeding a specific range (such as 3 mm), the patient's treatment can be carried out as shown in FIG. 8. As shown in FIG. 9(a), open the virtual radiation field on the side of the treatment couch. It can be seen that the virtual radiation field (purple) is completely included in PTV (green). FIG. 9(b) is shot at the end of the couch to simulate the shape of the beam and the patient treatment is performed.

By observing a patient (such as a breast cancer patient) who breathes to a specific position (indicated by the contour of body surface) and compares such position with the contour of the treatment plan, an active or passive method to hold the breath to perform the radiotherapy when there is a match. After a specific time, the patient breathes freely to repeat the process by holding the breath and perform the radiotherapy again. While the invention has been described by means of specific embodiments, numerous modifications and variations could be made thereto by those skilled in the art without departing from the scope and spirit of the invention set forth in the claims.

What is claimed is:

1. A research and development method of augmented reality in radiotherapy, comprising the steps of: (S1) scanning an image, by a CT scanner, wherein a CT scan of a patient is performed to obtain a DICOM image;
    (S2) preparing a radiotherapy plan, via a computing device, wherein the DICOM data obtained in the step (S1) are inputted into a treatment planning system, and a delineation of a planning target volume, a clinical target volume, and surrounding vital organs and tissues is carried out by a radiotherapist, and a virtual cube with the same dimensions (such as 16 cm*16 cm*16 cm) of the a cube calibration module is delineated, and the center of the virtual cube is set at the position of an isocenter of a tumor which is also situated at the isocenter of a radiotherapy accelerator, and a DICOM-RT data set is outputted;
    (S3) constructing a model, by the computing device, wherein the DICOM-RT data delineated in the step (S2) are inputted into a medical image processing software to carry out a three-dimensional reconstruction, and a certain transparency in the model is used to show a contour of body surface, a planning target volume, a clinical target volume and other surrounding organs and tissues, and then a 3D model is outputted in a common 3D processing software usable format;
    (S4) carrying out processing, by the computing device, wherein a 3D animation production software is used for making a material adjustment of a human 3D model, and then an augmented reality application program development software is introduced to adjust a material texture, and a light adjustment of the whole scene is made in the software;
    (S5) building a system, by the computing device, wherein an augmented reality interactive system is built, and then a real-time 3D virtual model motion is driven in a three-dimensional environment to achieve an augmented reality simulation;
    (S6) programming and performing an internal test, by the computing device: using a programming language to carry out functional programming in the augmented reality application development software, positioning the 3D virtual model in the system and realizing the translation and rotation of the X, Y and Z axis of the 3D virtual model, wherein a project file that is packaged and generated into a program file is tested internally in a mobile device to ensure a stable fluency of the program before use;
    (S7) positioning a virtual model, by the computing device, wherein a virtual cube of the virtual model and six-dimensional alignment method of the cube calibration module are used to realize the spatial position consistency between the 3D virtual model and the linear accelerator, so as to ensure that the 3D virtual model is positioned at the isocenter position;
    (S8) carrying out a clinical application via the computing device:
    wherein the cube calibration module is removed, and the patient to be treated clinically lies in a treatment couch of the accelerator, and the couch is lifted, translated, and rotated according to the positioning requirement of the radiotherapy to appropriately adjust the patient's treatment body position
    wherein a virtual radiation field is opened for verification and to match with the space of the early-stage 3D virtual model, so that the patient's body contour is detected by a laser radar scanner and the 3D virtual model are matched in a high degree for the treatment and
    resolve non-alignment between the estimated body contour position and direction of gravity to estimate the pose sequence by an inertial measurement unit (IMU), wherein the IMU calculates a predicted position element of the image frame, and the position of the feature point at the previous moment in the next image frame to improve the matching speed of the feature selection algorithm and quick rotation algorithm.

2. The method of augmented reality in radiotherapy as claimed in claim 1, wherein the scene needs to be rendered and baked in the step (S4).

3. The method of augmented reality in radiotherapy as claimed in claim 1, wherein the mobile end comprises a tablet device in the step (S5).

4. The method of augmented reality in radiotherapy as claimed in claim 1, wherein the 3D virtual model performing a space matching in the step (S8) specifically performs a body contour matching.

5. The method of augmented reality in radiotherapy as claimed in claim 1, wherein the treatment couch parameters and the patient's body position are adjusted appropriately in step (S8).

6. An apparatus for a research and development of augmented reality in radiotherapy, comprising
    a plurality of radiotherapy devices including an accelerator, and
    a 6D treatment couch,
    the at least one tablet device that comprises a motion sensor, a laser radar scanner and an inertial measurement unit (IMU),
    a corresponding supporting device of a camera,
    a memory, and
    one or more processors,
    wherein the one or more processors are configured to use the motion sensor, laser radar scanner, mobile device and camera to localize and map a human model to a 3D virtual model, and
    the one or more processors are configured to use the IMU to calculates a predicted position element of an image frame to resolve non-alignment between a body contour position and a direction of gravity.

* * * * *